United States Patent [19]

Ramsay et al.

[11] Patent Number: 5,112,854

[45] Date of Patent: May 12, 1992

[54] MACROLIDE COMPOUNDS

[75] Inventors: Michael V. J. Ramsay, South Harrow; Richard Bell, South Ruislip; Peter D. Howes; Edward P. Tiley, both of Pinner; Derek R. Sutherland, Chalfont St. Giles, all of England

[73] Assignee: American Cyanamid Company, Stamford, Conn.

[21] Appl. No.: 693,029

[22] Filed: Apr. 30, 1991

Related U.S. Application Data

[63] Continuation of Ser. No. 350,333, May 9, 1989, abandoned.

[30] Foreign Application Priority Data

May 10, 1988 [GB] United Kingdom ............... 8811037

[51] Int. Cl.⁵ ............... A61K 31/365; C07D 315/00
[52] U.S. Cl. ............................. 514/450; 549/264
[58] Field of Search .................... 514/450; 549/264

[56] References Cited

U.S. PATENT DOCUMENTS 4,806,527  2/1989  Christensen et al. ............ 549/264

FOREIGN PATENT DOCUMENTS 0259779  3/1988  European Pat. Off. .......... 549/264

Primary Examiner—C. Warren Ivy
Assistant Examiner—Amelia A. Owens
Attorney, Agent, or Firm—Bacon & Thomas

[57] ABSTRACT

Compounds of formula (1)

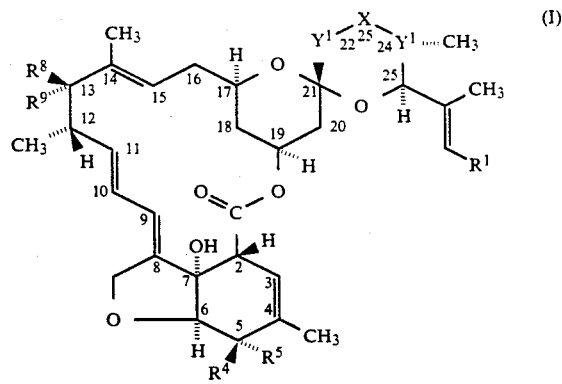

wherein $R^1$ represents a methyl, ethyl or isopropyl group; $Y^1$ is —$CH_2$—, $Y^2$ is —CH— and X represents

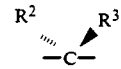

[where $R^2$ represents a hydrogen atom or a group $OR^6$ (where $OR^6$ is a hydroxy group or a substituted hydroxyl group having up to 25 carbon atoms) and $R^3$ represents a hydrogen atom, or $R^2$ and $R^3$ together with the carbon atom to which they are attached represent >C=O, >C=$CH_2$ or >C=$NOR^7$ (where $R^7$ represents a hydrogen atom, a $C_{1-8}$ alkyl group or a $C_{3-8}$ alkenyl group and the group >C=$NOR^7$ is in the E configuration)] or —$Y^1$—X—$Y^2$— represents —CH=CH—CH— or —$CH_2$—CH=C—; $R^4$ represents a group $OR^6$ as defined above and $R^5$ represents a hydrogen atom, or $R^4$ and $R^5$ together with the carbon atom to which they are attached represent >C=O or >C=$NOR^{7a}$ (where $R^{7a}$ is as defined above for $R^7$); and one of $R^8$ and $R^9$ represents an alkoxyalkoxy group optionally interrupted by an oxygen atom or an alkoxy group and the other represents a hydrogen atom or $R^8$ and $R^9$ together with the carbon atom to which they are attached represent >C=$NOR^{7b}$ (where $R^{7b}$ is as defined above for $R^7$), and salts thereof.

These compounds may be used to control nematode, acarine, insect or other pests.

9 Claims, No Drawings

MACROLIDE COMPOUNDS

This application is a continuation of application Ser. No. 07/350,333, filed May 9, 1989, now abandoned.

This invention relates to novel macrolide compounds, to processes for their preparation and to compositions containing them.

Thus, in one aspect, the invention particularly provides the compounds of formula (I):

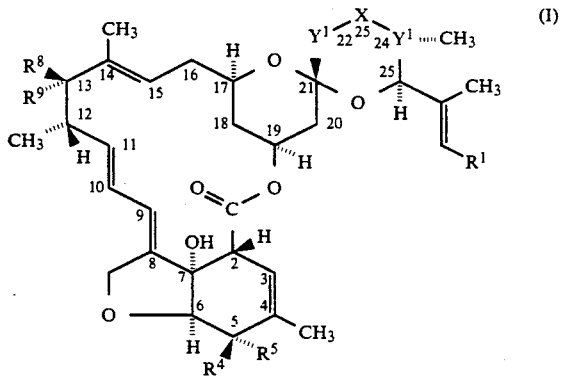

wherein $R^1$ represents a methyl, ethyl or isopropyl group;

$Y^1$ is $-CH_2-$, $Y^2$ is $-CH-$ and X represents

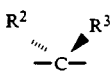

[where $R^2$ represents a hydrogen atom or a group $OR^6$ (where $OR^6$ is a hydroxy group or a substituted hydroxyl group having up to 25 carbon atoms) and $R^3$ represents a hydrogen atom, or $R^2$ and $R^3$ together with the carbon atom to which they are attached represent $>C=O$, $>C=CH_2$ or $>C=NOR^7$ (where $R^7$ represents a hydrogen atom, a $C_{1-8}$ alkyl group or a $C_{3-8}$ alkenyl group and the group $>C=NOR^7$ is in the E configuration)] or $-Y^1-X-Y^2-$ represents $-CH=CH-CH-$ or $-CH_2-CH=C-$;

$R^4$ represents a group $OR^6$ as defined above and $R^5$ represents a hydrogen atom, or $R^4$ and $R^5$ together with the carbon atom to which they are attached represent $>C=O$ or $>C=NOR^{7a}$ (where $R^{7a}$ is as defined above for $R^7$); and one of $R^8$ and $R^9$ represents an alkoxyalkoxy group optionally interrupted by an oxygen atom or an alkoxy group and the other represents a hydrogen atom or $R^8$ and $R^9$ together with the carbon atom to which they are attached represent $>C=NOR^{7b}$ (where $R^{7b}$ is as defined above for $R^7$), and salts thereof.

Compounds of formula (I) are of use as antibiotics. The compounds of the invention are also useful as intermediates in the preparation of further active compounds. When the compounds of formula (I) are to be used as intermediates, the group $-OR^6$ when present will often be a protected hydroxy group.

When $R^8$ or $R^9$ represents an alkoxyalkoxy group optionally interrupted by an oxygen atom or an alkoxy group it may be for example a $C_{1-6}$ alkoxy $C_{1-6}$ alkoxy group optionally interrupted by an oxygen atom or a $C_{1-6}$ alkoxy group.

The group $R^6$ when present in compounds of formula (I) may represent an acyl group e.g. a group of the formula $R^{10}CO-$ or $R^{10}OCO-$ (where $R^{10}$ is an aliphatic, araliphatic or aromatic group, for example an alkyl, alkenyl, alkynyl, cycloalkyl, aralkyl or aryl group), a formyl group, a group $R^{11}$ which is as defined above for $R^{10}$, a group $R^{12}SO_2-$ (where $R^{12}$ is a $C_{1-4}$ alkyl or $C_{6-10}$ aryl group), a silyl group, a cyclic or acyclic acetal group, a group $-CO(CH_2)_nCO_2R^{13}$ (where $R^{13}$ is a hydrogen atom or a group as defined above for $R^{10}$ and n represents zero, 1 or 2) or a group $R^{14}R^{15}NCO-$ (where $R^{14}$ and $R^{15}$ may each independently represent a hydrogen atom or a $C_{1-4}$alkyl group).

Where $R^{10}$ or $R^{11}$ are alkyl groups, they may be for example $C_{1-8}$ alkyl groups, e.g. methyl, ethyl, n-propyl, i-propyl, n-butyl, i-butyl, t-butyl or n-heptyl, which alkyl groups may also be substituted. Where $R^{10}$ is a substituted alkyl group it may be substituted by, for example, one or more halogen atoms (e.g. chlorine or bromine atoms), or a carboxy, $C_{1-4}$ alkoxy (e.g. methoxy, ethoxy), phenoxy or silyloxy group. Where $R^{11}$ is a substituted alkyl group it may be substituted by a cycloalkyl e.g. cyclopropyl group.

Where $R^{10}$ and $R^{11}$ are alkenyl or alkynyl groups, they preferably have 2-8 carbon atoms and where $R^{10}$ and $R^{11}$ are cycloalkyl groups, they may be for example $C_{3-12}$cycloalkyl, such as $C_{3-7}$cycloalkyl, e.g. cyclopentyl groups.

Where $R^{10}$ and $R^{11}$ are aralkyl groups, they preferably have 1-6 carbon atoms in the alkyl moiety, and the aryl group(s) may be carbocyclic or heterocyclic and preferably contain 4-15 carbon atoms e.g. phenyl. Examples of such groups include phen$C_{1-6}$alkyl e.g. benzyl groups.

Where $R^{10}$ and $R^{11}$ are aryl groups, they may be carbocyclic or heterocyclic and preferably have 4-15 carbon atoms e.g. phenyl.

When $R^6$ is a group $R^{12}SO_2-$, it may be for example a methylsulphonyl or p-toluenesulphonyl group.

Where $R^6$ represents a cyclic acetal group, it may for example have 5-7 ring members as in the tetrahydropyranyl group.

When $R^6$ represents a silyl group or $R^{10}$ contains a silyloxy substituent, the silyl moiety may carry three groups, which may be the same or different, selected from alkyl, alkenyl, alkoxy, cycloalkyl, aralkyl, aryl and aryloxy groups. Such groups may be as defined above for $R^6$ and particularly include methyl, t-butyl and phenyl groups. Particular examples at such silyloxy groups are trimethylsilyloxy and t-butyldimethylsilyloxy.

Where $R^6$ represents a group $-CO(CH_2)_nCO_2R^{13}$, it may for example be a group $-COCO_2R^{13}$ or $-COCH_2CH_2CO_2R^{13}$ where $R^{13}$ represents a hydrogen atom or a $C_{1-4}$alkyl group (e.g. methyl or ethyl).

When $R^6$ represents a group $R^{14}R^{15}NCO-$, $R^{14}$ and $R^{15}$ for example may each independently be a hydrogen atom or a methyl or ethyl group.

Where $R^7$ or $R^{7a}$ or $R^{7b}$ represents a $C_{1-8}$ alkyl group, it may be for example a methyl, ethyl, n-propyl, i-propyl, n-butyl, i-butyl or t-butyl group, and is preferably a methyl group.

When $R^7$ or $R^{7a}$ represents a $C_{3-8}$alkenyl group it may be for example an allyl group.

Where $R^8$ or $R^9$ represents a $C_{1-6}$ alkoxy group, it may be for example a methoxy, ethoxy, n-propoxy, i-propoxy, n-butoxy, i-butoxy or t-butoxy group, and is preferably a methoxy group.

Where $R^8$ or $R^9$ represents a $C_{1-6}$ alkoxy $C_{1-6}$ alkoxy group optionally interrupted by an oxygen atom, it may be for example a methoxy $C_{1-6}$ alkoxy group optionally interrupted by an oxygen atom, and is preferably a group —OCH$_2$OCH$_2$CH$_2$OCH$_3$.

Compounds of formula (I) containing an acidic group may form salts with bases. Examples of such salts include alkali metal salts such as sodium and potassium salts.

In the compounds of formula (I) $R^1$ preferably represents an isopropyl group.

An important group of compounds of formula (I) is that in which $Y^1$ is —CH$_2$—, $Y^2$ is —CH—, and X represents

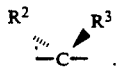

A further important group of compounds of formula (I) is that in which $R^4$ is a hydroxy, methoxy or acyloxy (e.g. acetyloxy) group or $R^4$ and $R^5$ together with the carbon atom to which they are attached represent >C=NOCH$_3$. $R^4$ preferably represents a hydroxyl group.

In a particular preference, $R^1$ in the compounds of formula (I) is an isopropyl group, $Y^1$ is —CH$_2$—, $Y^2$ is —CH—, X is

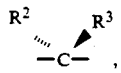

in which $R^2$ is a hydroxy, ethoxy or acetyloxy group and $R^3$ is hydrogen atom, or $R^2$ and $R^3$ together with the carbon atom to which they are attached represents >C=O, >C=CH$_2$ or >C=NOCH$_3$ (where the group >C=NOCH$_3$ is in the E configuration), or $R^2$ and $R^3$ each represents a hydrogen atom; $R^4$ is a hydroxy or acetoxy group and $R^5$ is a hydrogen atom; and one of $R^8$ and $R^9$ represents a methoxy group or a group —OCH$_2$OCH$_2$CH$_2$OCH$_3$ and the other represents a hydrogen atom or $R^8$ and $R^9$ together with the carbon atom to which they are attached represent >C=NOCH$_3$.

Important active compounds according to the invention are those of formula (I) in which:

$R^1$ is an isopropyl group, $Y^1$ is —CH$_2$—, $Y^2$ is —CH—, X represents —CH$_2$—, $R^4$ is a hydroxyl group, $R^5$ is a hydrogen atom, $R^8$ is a methoxy group and $R^9$ is a hydrogen atom;

$R^1$ is an isopropyl group, $Y^1$ is —CH$_2$—, $Y^2$ is —CH—, X represents >C=NOCH$_3$, $R^4$ is an acetoxy group, $R^5$ is a hydrogen atom, $R^8$ is a hydrogen atom and $R^9$ is a methoxy group;

$R^1$ is an isopropyl group, $Y^1$ is —CH$_2$—, $Y^2$ is —CH—, X represents >C=NOCH$_3$, $R^4$ is an acetoxy group, $R^5$ is a hydrogen atom, $R^8$ is a methoxy group and $R^9$ is a hydrogen atom; and $R^1$ is an isopropyl group, $Y^1$ is —CH$_2$—, $Y^2$ is —CH—, X represents >C=NOCH$_3$, $R^4$ is an acetoxy group, $R^5$ is a hydrogen atom, $R^8$ is a group —OCH$_2$OCH$_2$CH$_2$OCH$_3$ and $R^9$ is a hydrogen atom.

As indicated previously, compounds according to the invention may be of use as intermediates for the preparation of further active compounds. When the compounds of the invention are to be used as intermediates, the $R^4$ group may serve as a protecting group. It will be appreciated that such a protecting group should have the minimum of additional functionality to avoid further sites of reaction and should be selectively removable. Examples of groups serving as hydroxyl protecting groups are well known and are described, for example, in "Protective Groups in Organic Synthesis" by Theodora W. Greene. (Wiley-Interscience, New York 1981) and "Protective Groups in Organic Chemistry" by J. F. W. McOmie (Plenum Press, London, 1973). Examples of suitable $R^4$ protecting groups include phenoxyacetyl, silyloxyacetyl, (e.g. trimethylsilyloxyacetyl and t-butyldimethylsilyloxyacetyl), and silyl such as trimethylsilyl and t-butyldimethylsilyl. Compounds of the invention containing such groups will primarily be of use as intermediates. Other groups, such as acetyl, may serve as protecting groups, but may also be present in final active compounds.

Compounds of the invention have antibiotic activity e.g. antihelminthic activity, for example against nematodes, and in particular, anti-endoparasitic and anti-ectoparasitic activity.

The antibiotic activity of the compounds of formula (I) may, for example, be demonstrated by their activity against parasitic nematodes such as *Nematospiroides dubius*.

Ectoparasites and endoparasites infect humans and a variety of animals and are particularly prevalent in farm animals such as pigs, sheep, cattle, goats and poultry (e.g. chickens and turkeys), horses, rabbits, game-birds, caged birds, and domestic animals such as dogs, cats, guinea pigs, gerbils and hamsters. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Necator, Nematodirus, Nematospiroides (Heligomoroides), Nippostrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Triodontophorus, Uncinaria and Wuchereria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Chorioptes, Culliphore, Demodex, Damalinia, Dermatobia, Gastrophilus, Haematobia, Haematopinus, Haemophysalis, Hyaloma, Hypoderma, Ixodes, Linognathus, Lucilia, Melophagus, Oestrus, Otobius, Otodectes, Psorergates, Psoroptes, Rhipicephalus, Sarcoptes, Stomoxys and Tabanus.

Furthermore, the compounds of formula (I) are also of use in combating insect, acarine and nematode pests in agriculture, horticulture, forestry, public health and stored products. Pests of soil and plant crops, including cereals (e.g. wheat, barley, maize and rice) vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae, Aulacorthum circumflexum, Myzus persicae, Uephotettix cincticeps, Nilparvata*

*lugens, Panonychus ulmi, Phorodon humuli, Phyllocoptruta oleivora, Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius*; flour beetles such as *Tribolium castaneum*; flies such as *Musca domestica*; fire ants; leaf miners; *Pear psylla*; *Thrips tabaci*; cockroaches such as *Blatella germanica* and *Periplaneta americana* and mosquitoes such as *Aedes aegypti.*

According to the invention we therefore provide the compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or other vegetation) or to the pests themselves or a locus thereof.

The compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, implant, ophthalmic, nasal or genito-urinary use.

The compounds of formula (I) may be formulated for use in veterinary or human medicine according to the general methods described in UK Patent Specification 2166436.

The total daily dosages of the compounds of the invention employed in both veterinary and human medicine will suitably be in the range 1-2000 μg/kg bodyweight, preferably from 50-1000 μg/kg and these may be given in divided doses, e.g. 1-4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers and dilutents are as described in UK Patent Specification 2166436.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

The rate at which a compound is applied depends upon a number of factors including the type of pest involved and the degree of infestation. However, in general, an application rate of 10 g/ha to 10 kg/ha will be suitable; preferably from 10 g/ha to 1 kg/ha for control of mites and insects and form 50 g/ha to 10 kg/ha for control of nematodes.

The antibiotic compounds of the invention may be administered or used in combination with other active ingredients.

The compounds according to the invention may be prepared by a number of processes as described in the following where $R^1$-$R^9$, X, $Y^1$ and $Y^2$ are as defined for general formula (I) unless specified otherwise. In some of these processes it may be necessary to protect a hydroxyl group at the 5-, 13- and/or 23-position in the starting material prior to effecting the reaction described. In such cases it may then be necessary to deprotect the same hydroxyl group once the reaction has occurred to obtain the desired compound of the invention. Conventional methods of protection and deprotection may be used, for example as described in the aforementioned books by Greene and McOmie.

According to one process (A), a compound of formula (I) in which $R^8$ and $R^9$ together with the carbon atom to which they are attached represent $>C=NOR^{7b}$ (where $R^{7b}$ is an previously defined) may be prepared from a compound of formula (II)

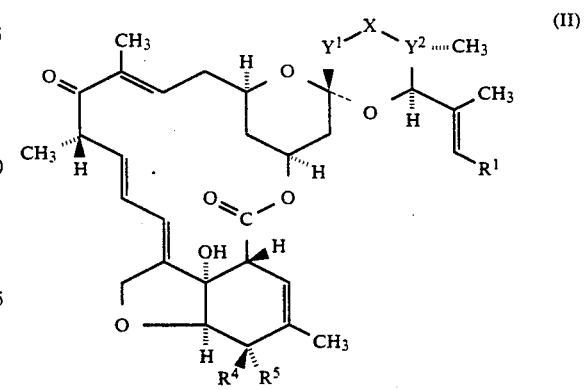

(wherein $R^4$ represents a group $OR^6$ where $OR^6$ is as previously defined or represents a protected hydroxyl group e.g. acetoxy) by reaction with a reagent $H_2NOR^{7b}$ (where $R^{7b}$ is as previously defined) or a salt thereof followed, if necessary, by removal of any protecting groups present.

The oximation reaction may conveniently be effected at a temperature in the range $-20°$ to $+100°$ C., e.g. $-10°$ to $+50°$ C. It is convenient to use the reagent $H_2NOR^{7b}$ in the form of a salt, for example an acid addition salt such as the hydrochloride. When such a salt is employed the reaction may be carried out in the presence of an acid binding agent.

Solvents which may be employed include alcohols (e.g. methanol or ethanol), amides (e.g. N,N-dimethylformamide, N,N-dimethylacetamide or hexamethylphosphoramide), ethers (e.g. cyclic cyclic ethers such as tetrahydrofuran or dioxan, and acylic ethers such as dimethoxyethane or diethylether), nitriles (e.g. acetonitrile), sulphones (e.g. sulpholane) and hydrocarbons such as halogenated hydrocarbons (e.g. methylene chloride), as well as mixtures of two or more such solvents. Water may also be employed as a cosolvent.

When aqueous conditions are employed the reaction may conveniently be buffered with an appropriate acid, base or buffer.

Suitable acids include mineral acids, such as hydrochloric or sulphuric acid, and carboxylic acid such as acetic acid. Suitable bases include alkali metal carbonates and bicarbonates such as sodium bicarbonate, hydroxides such as sodium hydroxide, and alkali metal carboxylates such as sodium acetate. A suitable buffer is sodium acetate/acetic acid.

According to another process (B), a compound of formula (I) in which $R^8$ or $R^9$ represents an alkoxyalkoxy group optionally interrupted by an oxygen atom or an alkoxy group may be prepared from a compound of formula (III)

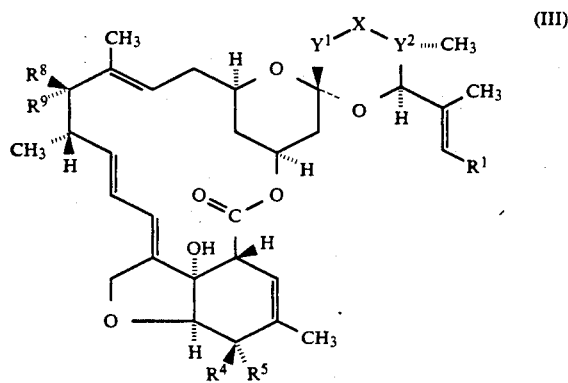

(III)

(wherein one of $R^8$ and $R^9$ represents a hydroxyl group and the other represents a hydrogen atom and $R^4$ represents a group $OR^6$ where $OR^6$ is as previously defined or represents a protected hydroxyl group e.g. acetoxy) by reaction with an etherifying agent, followed, if necessary, by removal of any protecting groups present.

Etherification may be effected using a reagent of formula $R^{ay}$ (where $R^a$ is an alkyl group or an alkoxyalkyl group optionally interrupted by an oxygen atom and Y represents a leaving group such a a halogen atom (e.g. chlorine, bromine or iodine) or a hydrocarbylsulphonyloxy group (e.g. mesyloxy or tosyloxy) or a haloalkanoyloxy group (e.g. dichloroacetoxy). When the etherification reaction is carried out using a halide it is preferable that a suitable base such as an amine (e.g. diisopropylethylamine) is also present.

Etherification may also be effected using a trialkyloxonium salt (e.g. a trialkyloxonium tetrafluoroborate salt), preferably in the presence of a suitable base e.g. 1,8-bis(dimethylamino)napthalene.

Solvents which may be employed in the above etherification reactions include ethers such as diethyl ether and hydrocarbons such as halogenated hydrocarbons (e.g. dichloromethane). The reaction may conveniently be carried out at a temperature in the range of 0° to 50° C., preferably at room temperature.

In yet another process (C), a compound of formula (I) in which $R^4$ is a hydroxyl group may be prepared from a corresponding compound of formula (I) in which $R^4$ is a substituted hydroxyl group. The conversion will usually be carried out in the context of removing a protecting group such as referred to above.

Thus, deprotection of the compounds of the invention in which $R^4$ represents a protected hydroxyl group can be effected by conventional methods, for example those extensively described in the aforementioned textbooks of McOmie and Greene. Thus, for example, when $R^4$ is an acyloxy group such as an acetoxy group the acetyl group may be removed by basic hydrolysis, e.g. using sodium or potassium hydroxide or ammonia in an aqueous alcohol such as methanol to yield the compound of formula (I) in which $R^4$ is a hydroxyl group.

In a further process (D), the compounds of the invention in which $OR^6$ is a substituted hydroxyl group may generally be prepared by reacting the corresponding 5 and/or 23-hydroxy compound with reagents serving to form a substituted hydroxyl group, followed, if necessary, by removal of any protecting groups present.

The reaction will in general be an acylation, sulphonylation, etherification, silylation, or acetalation, and the reaction may be effected according to the general methods described in UK Patent Specification 2176182. It will be appreciated that the etherification reaction may be carried out on a compound of formula (III) to provide in one step a compound of formula (I) in which $OR^6$ is alkoxy group and one of $R^8$ and $R^9$ is an alkoxy group and the other is a hydrogen atom.

In a further process (E), a compound of formula (I) in which X

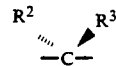

is and $R^2$ and $R^3$ together with the carbon atom to which they are attached represent $>C=O$ may be prepared by oxidising a corresponding compound of formula (I) wherein $R^2$ is a hydroxyl group and $R^3$ is a hydrogen atom, followed, if necessary, by removal of any protecting groups present. The reaction may be effected with an oxidising agent serving to convert a secondary hydroxyl group to an oxo group, whereby a compound of formula (I) is produced.

Suitable oxidising agents include quinones in the presence of water, e.g. 2,3-dichloro-5,6-dicyano-1,4-benzoquinone or 2,3,5,6-tetrachloro-1,4-benzoquinone; a chromium (VI) oxidising agent, e.g. pyridinium dichromate or chromium trioxide in pyridine; a manganese (IV) oxidising agent, e.g. manganese dioxide in dichloromethane; an N-halosuccinimide, e.g. N-chlorosuccinimide or N-bromosuccinimide; a dialkylsulphoxide e.g. dimethylsulphoxide, in the presence of an activating agent such as N,N'-dicyclohexylcarbodiimide or an acyl halide, e.g. oxalyl chloride; or a pyridine-sulphur trioxide complex.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate or a substituted amide e.g. dimethylformamide. Combinations of such solvents either alone or with water may also be used. The choice of solvent will depend on the oxidising agent used to effect the conversion.

The reaction may be carried out at a temperature of from $-80°$ C. to $+50°$ C.

In another process (F), a compound of formula (I) in which X is $>C=NOR^7$ may be prepared from the corresponding 23-keto compound of formula (I) in which X is >C=O by reaction with a reagent H₂NOR⁷ (where R⁷ is as defined previously). The reaction is preferably carried out using about one equivalent of the reagent H₂NOR⁷ and may conveniently be effected using the conditions described in process (A) above.

In a particular embodiment of this process, compounds of formula (I) in which X represents >C=NOR⁷ and R⁸ and R⁹ together with the carbon atom to which they are attached represent >C=NOR⁷ᵇ may be prepared from compounds of formula (II) in which X represents >C=O using two equivalents of the reagent H₂NOR⁷ under the conditions described in process (A) above. It will be appreciated that in the preparation of 13,23-bisoximes of formula (I) from corresponding 13,23-diketones the groups >C=NOR⁷ and >C=NOR⁷ᵇ will be equivalent.

In a further process (G), a compound of formula (I) in which X is a group >C=CH₂ may be prepared by reaction of a corresponding compound of formula (I) in which X is >C=O with an appropriate Witting reagent e.g. a phosphorane of formula (R¹⁶)₃P=CH₂ (where R¹⁶ is C₁₋₆ alkyl or aryl, e.g. monocyclic aryl such as phenyl). Suitable reaction solvents include ethers such as tetrahydrofuran or diethyl ether or a dipolar aprotic solvent such as dimethylsulphoxide. The reaction may be carried out at any suitable temperature e.g. at 0° C.

Intermediate compounds of formula (II) in which R⁴ is substituted hydroxyl group may be prepared from a compound of formula (III) in which R⁴ is a substituted hydroxyl group by oxidation. Suitable oxidising agents for the conversion include dialkylsulphoxides, e.g. dimethylsulphoxide, in the presence of an activating agent such as N,N'-dicyclohexylcarbodiimide or an acyl halide e.g. oxalyl chloride. The reaction may conveniently be effected in a suitable solvent such as a halogenated hydrocarbon, e.g. dichloromethane, at a temperature in the range of −80° to +50° C.

Intermediate compounds of formula (II) in which R⁴ is a hydroxy group may be prepared from the corresponding compounds of formula (II) in which R⁴ is a substituted hydroxyl group using the methods described above for the preparation of compounds of formula (I) in which R⁴ is a hydroxyl group.

Intermediate compounds of formula (III) in which R⁸ is a hydroxyl group and R⁹ is a hydrogen atom may be prepared by oxidising a compound of formula (IV)

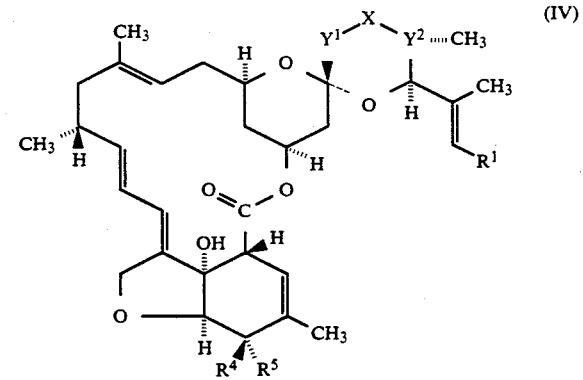

The oxidation may be effected for example with an oxidising agent such as selenium dioxide, preferably in the presence of an activator such as a peroxide, e.g. tert-butyl hydroperoxide. The reaction may conveniently be effected in an inert solvent such as a halogenated hydrocarbon e.g. dichloromethane, an ester, e.g. ethyl acetate or an ether, e.g. tetrahydrofuran, at a temperature in the range of 0° to 50° C., preferably at room temperature.

Alternatively, a compound of formula (IV) may be treated with an oxidising agent described above in formic acid at a temperature of from 20° to 100° C. e.g. 60° C. to provide a compound of formula (V).

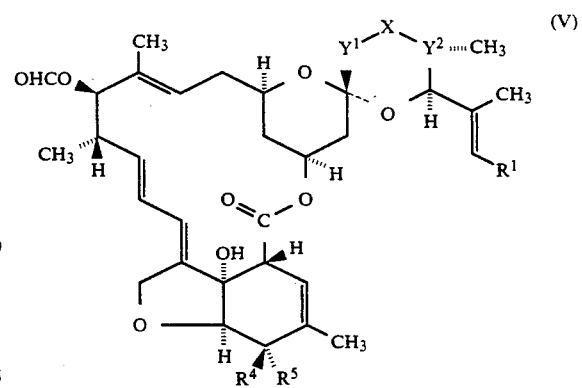

which, upon acid hydrolysis, e.g. using hydrochloric acid provides a compound of formula (III).

Intermediate compounds of formula (III) in which R⁸ is a hydrogen atom and R⁹ is a hydroxyl group may be prepared by reducing a compound of formula (II).

The reduction may be effected for example using a reducing agent such as a borohydride, for example an alkali metal borohydride such as sodium borohydride or a lithium alkoxyaluminium hydride such as lithium tributoxyaluminium hydride.

The reaction involving a borohydride reducing agent takes place in the presence of a solvent such as an alkanol e.g. isopropyl alcohol or isobutyl alcohol conveniently at a temperature in the range of −30° to +80° C. e.g. at 0° C. The reaction involving a lithium alkoxyaluminium hydride takes place in the presence of a solvent such as an ether e.g. tetrahydrofuran or dioxan conveniently at a temperature in the range of −78° to 0° C. e.g. at −78° C.

Intermediate compounds of formula (IV) in which Y¹ is —CH₂—, Y² is —CH— and X represents

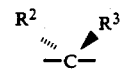

(where R² is a hydrogen atom or a group OR⁶ and R³ is a hydrogen atom or R² and R³ together with the carbon atom to which they are attached represent >C=O), R⁴ is a group OR⁶ and R⁵ is a hydrogen atom are known compounds described in UK Patent Specifications 2166436 and 2176182.

Intermediate compounds of formula (IV) in which —Y¹—X—Y²— represents —CH=CH—CH— or CH₂—CH=C—, R⁴ is a group OR⁶ and R⁵ is a hydrogen atom are known compounds described in European Patent Specification 215654.

Intermediate compounds of formula (IV) in which Y¹ is —CH₂—, Y² is —CH— and X represents >C=CH₂ may be prepared by reaction of a corresponding compound of formula (IV) in which X is >C=O with an appropriate Witting reagent according to the method of process (G) above.

Intermediate compounds of formula (IV) in which $Y^1$ is —CH$_2$—, $Y^2$ is —CH—, X represents >C=NOR$^7$ (where R$^7$ is as previously defined), R$^4$ is a group OR$^6$ and R$^5$ is a hydrogen atom or R$^4$ and R$^5$ together with the carbon atom to which they are attached represent >C=O, or intermediates in which X represents a group

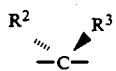

(where R$^2$ is a hydrogen atom or a group OR$^6$ and R$^3$ is a hydrogen atom) or X represents >C=NOR$^7$ or —Y$^1$—X—Y$^2$— represents —CH=CH—CH— or —CH$_2$—CH=C— and R$^4$ and R$^5$ together with the carbon atom to which they are attached represent >C=NOR$^{7a}$ may be prepared from the corresponding 5 and/or 23-keto compounds of formula (IV) by reaction with a reagent H$_2$NOR$^7$ using the oximation reaction conditions described above. It will be appreciated that in the preparation of a 5,23-bisoxime of formula (IV) from a corresponding 5,23-diketone the groups >C=NOR$^7$ and >C=NOR$^{7a}$ will be equivalent.

Intermediates of formula (IV) in which R$^4$ and R$^5$ together with the carbon atom to which they are attached represent >C=O may be prepared by oxidation of the corresponding 5-hydroxy compounds in which R$^4$ is a hydroxy group.

The reaction may be effected with an oxidising agent serving to convert an allylic secondary hydroxyl group to an oxo group, whereby a compound of formula (IV) is produced.

Suitable oxidising agents include, for example, transition metal oxides, such as manganese dioxide, and atmospheric oxygen in the presence of a suitable catalyst such as a finely divided metal e.g. platinum.

The oxidising agent will generally be used in excess over the stoichiometric quantity.

The reaction may conveniently be effected in a suitable solvent which may be selected from a ketone, e.g. acetone; an ether, e.g. diethyl ether, dioxan or tetrahydrofuran; a hydrocarbon, e.g. hexane; a halogenated hydrocarbon e.g. chloroform or methylene chloride; or an ester, e.g. ethyl acetate. Combinations of such solvents either alone or with water may also be used.

The reaction may be carried out at a temperature of from —50° C. to +50° C., preferably from 0° to 30° C.

It will be apprciated that the processes described above for preparing intermediate compounds of formula (IV) may also be utilised for the preparation of corresponding compounds of formulae (I), (II) and (III) and the present invention extends to cover such processes.

Intermediate compounds of formula (V) are novel compounds and constitute a further aspect of the present invention.

The compounds of formula (V) may, in general, be prepared by oxidising a corresponding compound of formula (IV). The oxidation may be effected for example using an oxidising agent such as selenium dioxide in formic acid at a temperature in the range of 20° to 100° C., e.g. 60° C.

Intermediate compounds of formula (V) in which X represents the group >C=NOR$^7$ may also be prepared from a corresponding compound of formula (V) in which X represents the group >C=O by reaction with a reagent H$_2$NOR$^7$ using the method of process (F) described above.

The invention is further illustrated by the following Preparations and Examples wherein the compound of formula (IV) above in which R$^1$ is isopropyl, $Y^1$ is —CH$_2$—, $Y^2$ is —CH—, X represents

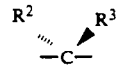

(where R$^2$ is a hydroxyl group and R$^3$ is a hydrogen atom), R$^4$ is a hydroxyl group and R$^5$ is a hydrogen atom is referred to as 'Factor A'. Compounds according to the invention are named with respect to Factor A. All temperatures are in 0° C.

INTERMEDIATE 1

(13R)-Hydroxy-23-desoxy Factor A, 5-acetate

23-Desoxy Factor A, 5-acetate (4.79 g, Example 112 in UK Patent Specification 2176182) was added to a stirred mixture of selenium dioxide (416 mg) and t-butyl hydroperoxide (3M in dichloromethane; 5 ml) in dichloromethane (30 ml). After stirring at room temperature for 30 h the reaction mixture was diluted with ethyl acetate (200 ml), washed with water and brine, and dried (Na$_2$SO$_4$). The solvent was evaporated and the residue purified by chromatography (250 g silica gel, Merck 9385). Elution with ethyl acetate: light petroleum (1:4→1:2) afforded the title compound (560 mg) as a pale yellow foam; $\nu_{max}$ (CHBr$_3$) 3600, 3460 (OH), 1732 (OAc), 1712 (CO$_2$R), 993 cm$^{-1}$ (C-O); δ(CDCl$_3$) values include 0.69 (3H, t, J 5 Hz), 2.15 (3H,s), 3.32 (1H,m), 3.72 (1H, d, J 10 Hz), 4.05 (1H, d, J 5 Hz), 5.52 (2H,m).

INTERMEDIATE 2

(13R)-Formyloxy-23-keto Factor A, 5-acetate

To a slurry of selenium dioxide (120 mg) in formic acid (1 ml) stirring at 60° was added a solution of 23-keto Factor A, 5-acetate (420 mg, Example 18 in UK Patent Specification 2176182) in formic acid (3 ml). The reaction mixture was left stirring at 60° for 6 mins then was poured into water. (150 ml) and extracted with diethyl ether (4×50 ml). The organic phase was dried (MgSO$_4$) and solvent removed to give a brown solid which was purified by medium pressure column chromatography on silica (100 g Merck kieselgel 60; 230-400 mesh). Elution with dichloromethane:ethyl acetate (16:1) gave the title compound as a cream foam (103 mg); $\nu$max (CHBr$_3$) 3480 (OH) and 1714 cm$^{-1}$ (ester and ketone); δ(CDCl$_3$) includes 0.86 (d, 6 Hz,3H), 0.97 (d,6 Hz, 3H), 1.02 (d,6 Hz,3H), 1.07 (d,6 Hz,3H), 1.76 (s,3H), 3.32 (m,1H), 2.16 (s,3H), 4.06 (d,6 Hz,1H), 5.02 (d,10 Hz,1H), 5.53 (m,2H), 8.08 (s,1H).

INTERMEDIATE 3

(13R)-Formyloxy-23(E)-methoxyimino Factor A, 5-acetate

To a solution of Intermediate 2 (80 mg) in methanol (8 ml) was added a solution of methoxyamine hydrochloride (29 mg) and sodium acetate (33 mg) in water (0.7 ml). The reaction mixture was left stirring at room temperature for 3 h, then was poured into ether (40 ml) and washed with water. The organic phase was dried (MgSO$_4$) and solvent removed to give the title compound as a cream foam (79 mg); δ(CDCl$_3$) includes 0.91 (d,6 Hz,3H), 0.97 (d,6 Hz,3H), 1.02 (d,6 Hz,3H), 1.07 (d,6 Hz,3H), 1.76 (s,3H), 2.16 (s,3H)m, 3.28 (d,15 Hz,1H), 1.91 (d,15 Hz,1H), 3.32 (m,1H), 3.83 (s,3H), 4.06 (d,6 Hz,1H), 5.04 (d,10 Hz,1H), 5.54 (m,2H), 8.09 (s,1H).

INTERMEDIATE 4

(13R)-Hydroxy-23(E)-methoxyimino Factor A, 5-acetate a) To a solution of Intermediate 3 (65 mg) in methanol (5 ml) was added 2N hydrochloric acid (0.1 ml). The reaction mixture was left stirring at room temperature for 4 h, then was poured into dichloromethane (60 ml) and washed with saturated sodium bicarbonate solution and water (40 ml of each). The organic phase was dried (MgSO$_4$) and solvent removed to give a foam (65 mg) which was purified by medium pressure column chromatography on silica (30 g, Merck Kieselgel 60, 230-400 mesh). Elution with dichloromethane:ethyl acetate (4:1) gave the title compound as a white foam (39 mg); [α]$_D^{21}$ +126° (C=0.22, CH$_2$Cl$_2$). δ(CDCl$_3$) includes 0.92 (d,6 Hz,3H), 0.96 (d,6 Hz,3H), 1.05 (d,6 Hz,3H), 1.12 (d,6 Hz,3H), 1.77 (s,3H), 2.17 (s,3H), 3.29 (d,15 Hz,1H), 1.91 (d,15 Hz,1H), 3.32 (m,1H), 3.70 (dd10,2 Hz,1H), 3.83 (s,3H), 4.04 (d,6 Hz,1H), 5.54 (m,2H).

b) To a slurry of selenium dioxide (460 mg) in formic acid (6 ml) stirring at 60° was added a solution of 23-keto Factor A, 5-acetate (1.80 g) in formic acid (16 ml). The reaction mixture was left stirring at 60° for 6 min, then was poured into water (500 ml) and extracted with diethyl ether (4×200 ml). The organic phase was dried (MgSO$_4$) and solvent removed to give a brown foam (1.89 g).

To a solution of this foam (1.89 g) in methanol (180 ml) was added a solution of methoxyamine hydrochloride (676 mg) and sodium acetate (760 mg) in water (16 ml). The reaction mixture was left stirring at room temperature for 3 h. Diethyl ether (700 ml) was added and the resulting mixture was washed with water. The organic phase was dried (MgSO$_4$) and the solvent removed to give a brown solid (1.89 g).

To a solution of this brown solid (1.89 g) in methanol (140 ml) was added 2N hydrochloric acid (3 ml) and the reaction mixture left stirring at room temperature for 2 h. Dichloromethane (1000 ml) was added and the solution was washed with saturated sodium bicarbonate solution, water and brine. The organic phase was dried (MgSO$_4$) and the solvent removed to give a brown foam (1.81 g) which was purified by medium pressure column chromatography (480 g, Merck Kieselgel 60, 230-400 mesh). Elution with dichloromethane:ethyl acetate (5:1) gave the title compound as a white foam (462 mg). Nmr as described above.

INTERMEDIATE 5

13-Keto-23(E)-methoxyimino Factor A, 5-acetate

To a solution of oxalyl chloride (0.24 ml) in freshly distilled dichloromethane (3.6 ml) stirring at −60° under nitrogen was added a solution of dimethyl sulphoxide (0.4 ml) in freshly distilled dichloromethane (3.6 ml). The solution was cooled to −65° and after 5 mins a solution of Intermediate 4 (770 mg) in dichloromethane (6 ml) was added. The cooling bath was allowed to warm to −60° then the reaction mixture left a further 30 min stirring at −60° to −50°. Triethylamine (1.5 ml) was added and the reaction mixture allowed to warm to room temperature. The reaction mixture was then poured into dichloromethane (100 ml) and the solvent removed under vacuum. Diethyl ether (60 ml) was added and the triethylamine salt filtered off. The ether was removed under vacuum to give a foam (760 mg) which was purified by medium pressure column chromatography on silica (180 g, Merck Kieselgel 60, 230-400 mesh). Elution with dichloromethane:ethyl acetate (14:1) gave the title compound as a beige foam (450 mg); δ(CDCl$_3$) includes 0.92 (d,6 Hz,3H), 0.96 (d,6 Hz,3H), 1.01 (d,6 Hz,3H), 1.18 (d,6 Hz,3H), 1.76 (s,3H), 1.80 (s,3H), 2.16 (s,3H), 3.31 (d,15 Hz, 1H), 1.93 (d,15 Hz,1H), 3.39 (m,1H), 3.84 (s,3H), 4.08 (d,6 Hz,1H), 5.54 (m,2H), 6.22 (t,9 Hz,1H).

INTERMEDIATE 6

(13S)-Hydroxy-23(E)-methoxyimino Factor A, 5-acetate

To a solution of Intermediate 5 (620 mg) in ethanol (25 ml) stirring at 0° was added a solution of sodium borohydride (4.9 ml of a 0.2M solution in ethanol). The reaction mixture was left stirring at 0° for 30 min, then was poured into ethyl acetate (400 ml) and washed with 2N hydrochloric acid, saturated sodium bicarbonate solution water and brine. The organic phase was dried (MgSO$_4$) and solvent removed to give a beige foam (605 mg) which was purified by medium pressure column chromatography on silica (180 g, Merck Kieselgel 60, 230-400 mesh). Elution with dichloromethane:ethyl acetate (10:1) gave the title compound as a white foam (502 mg); δ(CDCl$_3$) includes 0.92 (d,6 Hz,3H), 0.97 (d,6 Hz,3H), 1.05 (d,6 Hz,3H), 1.16 (d,6 Hz,3H), 1.76 (s,3H), 2.16 (s,3H), 3.29 (d,15 Hz,1H), 1.91 (d,15 Hz,1H), 3.32 (m,1H), 3.84 (s,3H), 4.00 (broad s,1H), 4.06 (d,6 Hz,1H), 5.53 (m,2H)

EXAMPLE 1

23-Desoxy-(13R)-methoxy Factor A, 5-acetate

A solution of Intermediate 1 (47.8 mg) in dichloromethane (2 ml) was treated with trimethyloxonium tetrafluoroborate (108 mg) and 1,8-bis(dimethylamino)-naphthalene (156 mg) under an atmosphere of nitrogen. After 22 h at room temperature, the reaction mixture was diluted with ethyl acetate (50 ml), washed with 2M hydrochloric acid, saturated sodium bicarbonate solution and brine, and dried (Na$_2$SO$_4$). The solvent was evaporated and the residue purified by flash chromatography (15 g silica gel, Merck 9385). Elution with ethyl acetate:petroleum ether (1:4) afforded the title compound as a pale yellow foam (32 mg); λ$_{max}$ (EtOH) 245.2 nm (ε29,600); ν$_{max}$ (CHBr$_3$) 1732 (OAc, 1710 cm$^{-1}$ (CO$_2$R); δ(CDCl$_3$) values include 0.69 (3H, d, J5 Hz), 0.94 (3H, d, J6 Hz), 1.04 (3H, d, J6 Hz), 1.08 (3H, d, J6 Hz), 1.76 (3H, s), 3.11 (1H, d, J10 Hz), 3.16 (3H, s), 3.32 (1H, m), 4.05 (1H, d, J6 Hz), 5.54 (2H, m).

EXAMPLE 2

23-Desoxy-(13 R)-methoxy Factor A

Aqueous sodium hydroxide (1M; 60 μl) was added to a solution of Example 1 (27 mg) in methanol (1 ml) at 0°. After 1.5 h at 0°, the reaction mixture was diluted with ethyl acetate (50 ml), washed with water and brine and dried (Na$_2$SO$_4$). The solvent was evaporated and the residue purified by flash chromatography (15 g silica gel, Merck 9385). Elution with ethyl acetate:light petroleum (1:3) afforded the title compound as a white foam (22.7 mg); $\lambda_{max}$(EtOH) 245 nm ($\epsilon$28,400); $\nu_{max}$(CHBr$_3$) 3540 (OH), 1708 cm$^{-1}$ (CO$_2$R); $\delta$(CDCl$_3$) values include 0.68 (3H, d, J3 Hz), 0.94 (3H, d, J6 Hz), 1.05 (3H, d, J6 Hz), 1.08 (3H, d, J6 Hz), 1.87 (3H, s), 3.11 (1H, d, J10 Hz), 3.16 (3H, s), 3.28 (1H,m) 3.96 (1H, d, J5 Hz), 4.29 (1H, t, 5 Hz).

EXAMPLE 3

(13R)-Methoxy-23(E)-methoxyimino Factor A,5-acetate

A mixture of Intermediate 4 (47 mg), trimethyloxonium tetrafluoroborate (106 mg) and 1,8-bis(dimethylamino)naphthalene (153 mg) in dichloromethane (0.4 ml) was stirred in an atmosphere of nitrogen at room temperature for 18 h. Ice-water (15 ml) was added and the mixture was extracted with ether (2×25 ml). The extracts were washed with 5% sodium hydrogen carbonate and water and dried. Removal of solvent gave a white gum which was purified by medium pressure column chromatography on silica (40 g, Merck Kieselgel 60, 230-400 mesh). Elution with dichloromethane:ether (6:1) gave the title compound as a white foam (26.5 mg); $[\alpha]_D^{22}+101°$ (C,0.4, CH$_2$Cl$_2$); $\lambda$max (EtOH) 245.2 and 277.8 nm ($\epsilon$22270 and 3270); $\nu$ (CHBr$_3$) 3480 (OH), 1738 (acetate) and 1712 cm$^{-1}$ (lactone); $\delta$(CDCl$_3$) includes 0.92 (d,6 Hz,3H), 0.97 (d,6 Hz,3H), 1.06 (d,6 Hz,3H), 1.09 (d,6 Hz,3H), 1.77 (s,3H), 1.92 (d,15 Hz,1H), 2.17 (s,3H), 3.09 (d,10 Hz, 1H), 3.16 (s,3H), 3.29 (d,15 Hz,1H), 3.32 (m,1H), 3.84 (s,3H), 4.04 (d,6 Hz,1H), 5.54 (m,2H).

EXAMPLE 4

(13R)-(2'-Methoxyethoxymethoxy)-23(E)-methoxyimino Factor A,5-acetate

A solution of 2-methoxyethoxymethyl chloride (55 mg) in dichloromethane (250 μl) was added with stirring to a mixture of diisopropylethylamine (153 μl) and Intermediate 4 (100 mg) in dichloromethane (250 μl). The mixture was maintained at ca 20° for 5 days. Ether (50 ml) was added and the mixture was washed with saturated sodium hydrogen carbonate and water and dried. Removal of solvent gave a yellow foam which was purified by medium pressure column chromatography on silica (80 g, Merck Kieselgel 60, 230-400 mesh). Elution with dichloromethane:ether (6:1) gave the title compound as a white foam (70 mg); $\lambda$max (EtOH) 245.2 and 277.4 nm ($\epsilon$25330 and 2695); $\nu$max (CHBr$_3$) 3540, 3420 (OH), 1736 (acetate) and 1712 cm$^{-1}$ (lactone); $\delta$(CDCl$_3$) includes 0.92 (d,6 Hz,3H), 0.98 (d,6 Hz,3H), 1.07 (d,6 Hz,3H), 1.10 (d,6 Hz,3H), 1.77 (s,3H), 1.91 (d, 15 Hz,1H), 2.16 (s,3H), 3.29 (d,15 Hz,1H), 3.32 (m,1H), 3.39 (s,3H), 3.83 (s,3H), 4.04 (d,6 Hz,1H), 4.5-4.8 (m,4H), 5.54 (m,2H).

EXAMPLE 5

13,23(E)-Bis(methoxyimino) Factor A, 5-acetate

A solution containing Intermediate 5 (56 mg), methoxyamine hydrochloride (43 mg) and anhydrous sodium acetate (41 mg) in methanol (10 ml) was stood at 20° for 2 days then evaporated to near dryness. The resultant mixture was shaken with ethyl acetate and water and the organic phase was washed successively with 0.5N hydrochloric acid and water. The dried organic phase was evaporated and the crude product was purified by chromatography over Merck Keiselgel 60, 230-400 mesh (80 ml). Elution of the column with hexane:ethyl acetate (3:1) afforded the title compound as a white foam (32 mg); $[\alpha]_D^{21}+61°$ (c 1.11, CHCl$_3$); $\lambda$max (EtOH) 247 nm ($\epsilon$31,400), $\lambda$max (CHBr$_3$) (cm$^{-1}$) 3480 (OH), 1732 (OAc) 1712 (CO$_2$R) $\delta$(CDCl$_3$) include 5.54 (m;2H), 5.14 (m;1H), 3.84 (s;3H), 3.81 (s;3H), 3.36 (m;1H), 3.29 (d15;1H), 3.14 (m;1H), 2.17 (s;3H), 1.91 (d15;1H), 1.76 (s;3H), 1.66 (s;3H), 1.63 (s;3H), 1.21 (d6;3H), 1.06 (d6;3H), 0.96 (d6;3H, 0.92 (d6;3H).

EXAMPLE 6

13,23(E)-Bis(methoxyimino) Factor A

A solution containing Example 5 (22 mg) and 1N sodium hydroxide (0.1 ml) in methanol (5 ml) was stirred in an ice bath for 1.3 h. The solution was diluted with ether (20 ml) and washed successively with 0.5N hydrochloric acid and water. The dried organic phase was evaporated to afford the title compound as an off-white foam (12 mg); $\nu$max (CHBr$_3$) (cm$^{-1}$) 3500 (OH), 1710 (C=O); $\delta$(CDCl$_3$) include 5.18 (d9;1H), 5.12 (m;1H), 4.30 (m;1H), 3.84 (s;3H), 3.81 (s;3H), 3.31 (m;1H), 3.28 (d14;1H), 3.12 (m;1H), 1.88 (s;3H), 1.66 (s;3H), 1.63 (s;3H), 1.19 (d6;3H), 1.05 (d6;3H), 0.96 (d6;3H), 0.91 (d6;3H).

EXAMPLE 7

(13S)-Methoxy-23(E)-methoxyimino Factor A, 5-acetate

To a sample of Intermediate 6 (107 mg) under nitrogen was added trimethyloxonium tetrafluoroborate (230 mg), 1,8-bisdimethylaminonaphthalene (330 mg) and dichloromethane (0.9 ml). The reaction mixture was left stirring at room temperature under nitrogen for 2 h, then the source of nitrogen removed. The reaction mixture was left stirring a further 72 h at room temperature then poured into water (30 ml) and extracted with diethyl ether (2×50 ml). The organic phase was washed with 2N hydrochloric acid, saturated sodium bicarbonate solution, water and brine and then dried (MgSO$_4$). Removal of solvent gave a yellow foam (55 mg) which was combined with the crude product (35 mg) from a similar reaction (using 47 mg of starting material). The material was purified by medium pressure column chromatography on silica (35 g, Merck Kieselgel 60, 230-400 mesh). Elution with dichloromethane:ethyl acetate (20:1) gave the title compound as a white foam (24 mg); $\delta$(CDCl$_3$) includes 0.92 (d,6 Hz,3H), 0.96 (d,6 Hz,3H), 1.06 (d,6 Hz,3H), 1.12 (d,6 Hz,3H), 1.77 (s,3H), 2.17 (s,3H), 3.28 (d,15 Hz,1H), 1.92 (d,15 Hz,1H), 3.32 (m,5H), 3.84 (s,3H), 4.06 (d,6 Hz,1H), 5.53 (m,2H).

EXAMPLE 8

(13S)-(2'-Methoxyethoxymethoxy)-23(E)-methoxyimino Factor A, 5-acetate

To a sample of Intermediate 6 (100 mg) was added a solution of N,N-diisopropylethylamine (153 μl) in dichloromethane (250 μl) followed by a solution of 2-methoxyethoxymethyl chloride (55 mg) in dichloromethane (250 μl). The reaction mixture was left stirring at room temperature for 140 h, then was poured into dichloromethane (50 ml) and washed with 2N hydrochloric acid, saturated sodium bicarbonate solution, water and brine. The organic phase was dried (MgSO$_4$) and solvent removed to give a beige solid (111 mg) which was purified by medium pressure column chromatography on silica (40 g, Merck Kieselgel 60, 230-400 mesh). Elution with dichloromethane:ethyl acetate (10:1) gave the title compound as a white foam (58 mg); $[\alpha]_D^{21} +77°$ (C=0.37, $CH_2Cl_2$); λmax (EtOH) 245.0 nm ε27900 ($E_1^1$ 355); νmax 3540+3450 (OH) 1732 (acetate) and 1710 cm$^{-1}$ (ester); δ($CDCl_3$) includes 0.91 (d,6 Hz,3H), 0.97 (d,6 Hz,3H), 1.06 (d,6 Hz,3H), 1.12 (d,6 Hz,3H), 1.76 (s,3H), 2.15 (s,3H), 3.29 (d,14 Hz,1H), 3.32 (m,1H), 3.39 (s,3H), 3.82 (s,3H), 3.93 (s,1H), 4.04 (d,6 Hz,1H), 4.67 (s,2H), 5.53 (m,2H).

The following are examples of formulations according to the invention. The term 'Active Ingredient' as used hereinafter means a compound of the invention.

MULTIDOSE PARENTERAL INJECTION

EXAMPLE 1

|  | % w/v | Range |
|---|---|---|
| Active ingredient | 2.0 | 0.1–6.0% w/v |
| Benzyl alcohol | 1.0 |  |
| Polysorbate 80 | 10.0 |  |
| Glycerol formal | 50.0 |  |
| Water for Injections to | 100.0 |  |

Dissolve the active ingredient in the polysorbate 80 and glycerol formal. Add the benzyl alcohol and make up to volume with Water for Injections. Sterilize the product by conventional methods, for example sterile filtration or by heating in an autoclave and package aseptically.

EXAMPLE 2

|  | % w/v | Range |
|---|---|---|
| Active ingredient | 4.0 | 0.1–7.5% w/v |
| Benzyl alcohol | 2.0 |  |
| Glyceryl triacetate | 30.0 |  |
| Propylene glycol to | 100.0 |  |

Dissolve the active ingredient in the benzyl alcohol and glyceryl triacetate. Add the propylene glycol and make up to volume. Sterilize the product by conventional pharmaceutical methods, for example sterile filtration, and package aseptically.

EXAMPLE 3

|  | % | Range |
|---|---|---|
| Active ingredient | 2.0 w/v | 0.1–7.5% w/v |
| Ethanol | 36.0 v/v |  |
| Non-ionic surfactant (e.g. Synperonic PE L44*) | 10.0 w/v |  |
| Propylene glycol to | 100.0 |  |

*Trademark of ICI

Dissolve the active ingredient in the ethanol and surfactant and make up to volume. Sterilize the product by conventional pharmaceutical methods, for example sterile filtration, and package aseptically.

EXAMPLE 4

|  | % | Range |
|---|---|---|
| Active Ingredient | 2.0 w/v | 0.1–3.0% w/v |
| Non-ionic surfactant (e.g. Synperonic PE F68*) | 2.0 w/v |  |
| Benzyl alcohol | 1.0 w/v |  |
| Miglyol 840** | 16.0 v/v |  |

-continued

|  | % | Range |
|---|---|---|
| Water for Injections to | 100.0 |  |

*Trademark of ICI
**Trademark of Dynamit Nobel

Dissolve the active ingredient in the Miglyol 840. Dissolve the non-ionic surfactant and benzyl alcohol in most of the water. Prepare the emulsion by adding the oily solution to the aqueous solution while homogenising using conventional means. Make up to volume. Aseptically prepare and package aseptically.

Aerosol spray

|  | % w/w | Range |
|---|---|---|
| Active Ingredient | 0.1 | 0.01–2.0% w/w |
| Trichloroethane | 29.9 |  |
| Trichlorofluoromethane | 35.0 |  |
| Dichlorodifluoromethane | 35.0 |  |

Mix the Active Ingredient with trichloroethane and fill into the aerosol container. Purge the headspace with the gaseous propellant and crimp the valve into position. Fill the required weight of liquid propellant under pressure through the valve. Fit with actuators and dust-caps.

Tablet

Method of manufacture—wet granulation

|  | mg |
|---|---|
| Active Ingredient | 250.0 |
| Magnesium stearate | 4.5 |
| Maize starch | 22.5 |
| Sodium starch glycolate | 9.0 |
| Sodium lauryl sulphate | 4.5 |
| Microcrystalline cellulose to tablet core weight of 450 mg | |

Add sufficient quantity of a 10% starch paste to the active ingredient to produce a suitable wet mass for granulation. Prepare the granules and dry using a tray or fluid-bed drier. Sift through a sieve, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

Veterinary tablet for small/domestic animal use

Method of manufacture—dry granulation

|  | mg |
|---|---|
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing granules. Compress into tablets.

The tablet cores can then be film-coated, if desired, as described above.

Veterinary intrammary injection

|  |  | mg/dose | Range |
|---|---|---|---|
| Active Ingredient |  | 150 mg | 0.05-1.0 g |
| Polysorbate 60 | 3.0% w/w | } to 3 g | } to 3 or 15 g |
| White Beeswax | 6.0% w/w | | |
| Arachis oil | 91.0% w/w | | |

Heat the arachis oil, white beeswax and polysorbate 60° to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

Veterinary slow-release bolus

|  | % w/w | Range |
|---|---|---|
| Active Ingredient |  | 0.25-2 g |
| Colloidal silicon dioxide | 2.0 | } to required fill weight |
| Microcrystalline cellulose to | 100.0 | |

Blend the active ingredient with the colloidal silicon dioxide and microcrystalline cellulose by using a suitable aliquot blending technique to achieve a satisfactory distribution of active ingredient throughout the carrier. Incorporate into the slow release device and give (1) a constant release of active ingredient or (2) a pulsed release of active ingredient.

Veterinary oral drench

|  | % w/v | Range |
|---|---|---|
| Active Ingredient | 0.35 | 0.01-2% w/v |
| Polysorbate 85 | 5.0 | |
| Benzyl alcohol | 3.0 | |
| Propylene glycol | 30.0 | |
| Phosphate buffer | as pH 6.0-6.5 | |
| Water to | 100.0 | |

Dissolve the active ingredient in the Polysorbate 85, benzyl alcohol and the propylene glycol. Add a proportion of the water and adjust the pH to 6.0-6.5 with phosphate buffer, if necessary. Make up to final volume with the water. Fill the product into the drench container.

Veterinary oral paste

|  | % w/w | Range |
|---|---|---|
| Active Ingredient | 4.0 | 1-20% w/w |
| Saccharin sodium | 2.5 | |
| Polysorbate 85 | 3.0 | |
| Aluminium distearate | 5.0 | |
| Fractionated coconut oil to | 100.0 | |

Disperse the aluminium distearate in the fractionated coconut oil and polysorbate 85 by heating. Cool to room temperature and disperse the saccharin sodium in the oily vehicle. Disperse the active ingredient in the base. Fill into plastic syringes.

Granules for veterinary in-feed administration

|  | % w/w | Range |
|---|---|---|
| Active Ingredient | 2.5 | 0.05-5% w/w |
| Calcium sulphate, hemi-hydrate to | 100.0 | |

Blend the Active Ingredient with the calcium sulphate. Prepare the granules using a wet granulation process. Dry using a tray or fluid-bed drier. Fill into the appropriate container.

Veterinary Pour-on

|  | % w/v | Range |
|---|---|---|
| Active Ingredient | 2.0 | 0.1 to 30% |
| Demethyl sulphoxide | 10.0 | |
| Methyl Isobutyl ketone | 30.0 | |
| Propylene glycol (and pigment) to | 100.0 | |

Dissolve the active ingredient in the dimethyl sulphoxide and the methyl isobutyl ketone. Add the pigment and make up to volume with the propylene glycol. Fill into the pour-on container.

Emulsifiable Concentrate

| Active ingredient | 50 g |
|---|---|
| Anionic emulsifier | 40 g |
| (e.g. Phenyl sulphonate CALX) | |
| Non-ionic emulsifier | 60 g |
| (e.g. SYNPERONIC NP13)* | |
| Aromatic solvent (e.g. Solvesso 100) to | 1 liter. |

*Trademark of ICI

Mix all ingredients, stir until dissolved.

Granules

| (a) Active ingredient | 50 g |
|---|---|
| Wood resin | 40 g |
| Gypsum granules (20-60 mesh) to | 1 kg |
| (e.g. Agsorb 100A) | |
| (b) Active ingredient | 50 g |
| SYNPERONIC NP13* | 40 g |
| Gypsum granules (20-60 mesh) to | 1 kg. |

*Trademark of ICI

Dissolve all ingredients in a volatile solvent e.g. methylene chloride, add to granules tumbling in mixer. Dry to remove solvent.

We claim:

1. Compounds of formula (1)

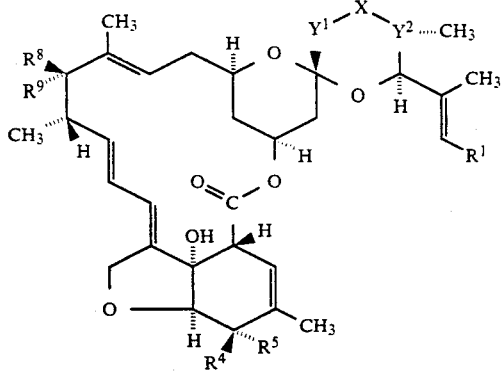 (I)

wherein $R^1$ represents a methyl, ethyl or isopropyl group;

$Y^1$ is $-CH_2-$, $Y^2$ is $-CH-$ and X represents

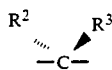

where $R^2$ and $R^3$ together with the carbon atom to which they are attached represents $>C=NOR^7$, where $R^7$ represents a hydrogen atom, a $C_{1-8}$ alkyl group or a $C_{3-8}$ alkenyl group and the group $>C=NOR^7$ is the E configuration, or $-Y^1-X-Y^2$ represents $-CH_2-CH=C-$;

$R^4$ represents an hydroxy, methoxy or acyloxy group and $R^5$ represents a hydrogen atom or $R^4$ and $R^5$ together with the carbon atoms to which they are attached represents $>C=O$ or $>C=NOR^{7a}$, where $R^{7a}$ is as defined above for $R^7$; and one of $R^8$ and $R^9$ represents $C_1$-$C_6$ alkoxy group optionally interrupted by an oxygen atom or a $C_1$-$C_6$ alkoxy group and the other represents a hydrogen atom or $R^8$ and $R^9$ together with the carbon atom to which they are attached represent $>C=NOR^{7b}$, where $R^{7b}$ is as defined above for $R^7$, and salts thereof.

2. Compounds according to claim 1 in which $R^1$ is an isopropyl group.

3. Compounds according to claim 1 in which $R^8$ or $R^9$ is a methoxy group or $-OCH_2OCH_2CH_2OCH_3$.

4. Compounds according to claim 1 in which $R^1$ is an isopropyl group, $Y^1$ is $-CH_2-$, $Y^2$ is $-CH-$, X is $-C(R^2)(R^3)-$, in which $R^2$ and $R^3$ together with the carbon atom to which they are attached represent $>C=CH_2$ or $>C=NOCH_3$ (where the group $>C=NOCH_3$ is in the E configuration), $R^4$ is a hydroxy or acetoxy group and $R^5$ is a hydrogen atom; and one of $R^8$ and $R^9$ represents a methoxy group or a group $-OCH_2OCH_2CH_2OCH_3$ and the other represents a hydrogen atom or $R^8$ and $R^9$ together with the carbon atom to which they are attached represent $>C=NOCH_3$.

5. Compounds according to claim 1 in which
$R^1$ is an isopropyl group, $Y^1$ is $-CH_2-$, $Y^2$ is $-CH-$, X represents $>C=NOCH_3-$, $R^4$ is an acetoxy group, $R^5$ is a hydrogen atom, $R^8$ is a hydrogen atom and $R^9$ is a methoxy group;

$R^1$ is an isopropyl group, $Y^1$ is $-CH_2-$, $Y^2$ is $-CH-$, X represents $>C=NOCH_3$, $R^4$ is an acetoxy group, $R^5$ is a hydrogen atom, $R^8$ is a methoxy group and $R^9$ is a hydrogen atom; and $R^1$ is an isopropyl group, $Y^1$ is $-CH_2-$, $Y^2$ is $-CH-$, X represents $>C=NOCH_3$, $R^4$ is an acetoxy group, $R^5$ is a hydrogen atom, $R^8$ is a group $-OCH_2OCH_2CH_2OCH_3$ and $R^9$ is a hydrogen atom.

6. A pharmaceutical composition containing a pesticidally effective amount of at least one compound as claimed in claim 1 together with a pharmaceutically acceptable carrier.

7. A veterinary composition containing a pesticidally effective amount of at least one compound as claimed in claim 1 and a veterinary acceptable carrier.

8. A pesticidal composition containing a pesticidally effective amount of a compound as claimed in claim 1 and a pesticidally acceptable carrier.

9. A method of controlling insect, acarine or nematode pests which comprises applying an amount of a compound according to claim 1 effective in combatting pests to the pests or a locus of said pests.

* * * * *